United States Patent
Hagg et al.

(10) Patent No.: US 9,283,030 B2
(45) Date of Patent: Mar. 15, 2016

(54) HF SURGICAL DEVICE

(75) Inventors: Martin Hagg, Wannweil (DE); Peter Selig, Nehren (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1107 days.

(21) Appl. No.: 13/025,892

(22) Filed: Feb. 11, 2011

(65) Prior Publication Data
US 2011/0202051 A1    Aug. 18, 2011

(30) Foreign Application Priority Data
Feb. 12, 2010   (DE) .................. 10 2010 000 396

(51) Int. Cl.
| | | |
|---|---|---|
| A61B 18/14 | (2006.01) | |
| A61B 18/12 | (2006.01) | |
| A61B 18/16 | (2006.01) | |

(52) U.S. Cl.
CPC ......... *A61B 18/1402* (2013.01); *A61B 18/1233* (2013.01); *A61B 2018/167* (2013.01)

(58) Field of Classification Search
CPC .............. A61B 18/12; A61B 18/1206; A61B 18/1233; A61B 2018/167; A61B 2018/00601; A61B 2018/00767

USPC ....................................................... 606/32–50
See application file for complete search history.

(56) References Cited

U.S. PATENT DOCUMENTS

| | | | |
|---|---|---|---|
| 4,121,590 A | 10/1978 | Gonser | |
| 4,788,977 A | 12/1988 | Farin et al. | |
| 5,246,438 A * | 9/1993 | Langberg | 606/33 |
| 5,312,401 A * | 5/1994 | Newton et al. | 606/46 |
| 2003/0050557 A1* | 3/2003 | Susil et al. | 600/424 |
| 2010/0023000 A1* | 1/2010 | Stevenson et al. | 606/33 |
| 2011/0160718 A1* | 6/2011 | Werner | 606/39 |

FOREIGN PATENT DOCUMENTS

WO    WO 2004/062516 A1    7/2004

* cited by examiner

Primary Examiner — Michael Peffley
(74) Attorney, Agent, or Firm — Dickstein Shapiro LLP

(57) ABSTRACT

An HF surgical device comprising an HF surgical generator, at least one surgical instrument having an active electrode and a neutral electrode, which are connectable to the HF generator. The surgical instrument is connectable to the HF generator via a first wire and the neutral electrode is connectable to the HF generator via second wire. The first and/or second wire is/are equipped with a shield and a decoupling capacitor is disposed at a distal end of each shielded wire.

3 Claims, 2 Drawing Sheets

HF SURGICAL DEVICE

FIELD OF THE INVENTION

Embodiments disclosed herein relate to a high-frequency (HF) surgical device having shielded wires and decoupling capacitors.

BACKGROUND

High-frequency (HF) surgical devices of the type addressed herein are well-known. They have an HF generator and at least one surgical instrument having an active electrode that is connected to the HF generator via a wire for supplying a high-frequency current. In addition, a neutral electrode is provided, which is likewise connected to the HF generator via a corresponding second wire for returning the current.

An HF generator of the type addressed herein generates a high-frequency electrical voltage or current and routes them to the connected surgical instrument via an appropriate wire. The surgical instrument may be a monopolar, bipolar or quasi-bipolar instrument for cutting and/or coagulating biological tissue. In addition, accessory devices for adjusting, monitoring, controlling, limiting and/or modulating the HF voltages, HF currents, electric arcs between an active electrode and a biological tissue that are required for cutting and/or coagulating, may be connected to the HF generator or be disposed within it.

However, requirements that are reflected for example, in the European Parliament's Directive 2004/40/EC of 29 Apr. 2004, governing the minimum specifications for protecting the health and safety of employees against hazards due to physical interference (e.g., electromagnetic fields), are associated with such HF surgical devices. In the case of HF surgical devices, the requirements mandate that the wires that lead to a patient be provided with shielding in order, among other things, to minimize the electrical fields arising due to the high-frequency current. A generic HF surgical device with shielded wires is disclosed in DE 91 17 217 U1. In this case, however, the use of shielded wires for connecting the surgical instrument to the HF generator, or for connecting the neutral electrode to the HF generator, is disadvantageous because it is associated with significant problems.

The use of shielded wires gives rise, in particular, to the problem that the shield forms a capacitive load that reduces the level of the output voltage between the surgical instrument and the tissue to be treated. This is unfortunate because the level of the high-frequency voltage present between the active electrode and the tissue to be treated is a decisive parameter for the desired HF surgery effect. Moreover, it is necessary, or specified by the pertinent standards, to provide what is known as a decoupling capacitor in the HF generator's output circuit to suppress the occurrence of direct current components that may be harmful to the patient.

Furthermore, using shielded wires also gives rise to the problem that the shielding of the wires is preferably grounded (also referred to as "earthed" or "earth grounded") and this ground connection promotes the occurrence of leakage currents at points where the patient is in contact with grounded, conductive parts; in particular, these leakage currents may become greater, which in turn has an adverse impact on the surgical effect and also represents a risk to the patient.

SUMMARY

An object of the embodiments of the disclosed herein is to create an HF surgical device that prevents or at least reduces the problems occurring when shielded wires are used; that is, on one hand the embodiments reduce the output voltage at the point where the surgical instrument is used and, on the other, they reduce the occurrence of leakage currents.

To achieve this object, an HF surgical device comprising an HF generator and at least one surgical instrument having an active electrode and a neutral electrode is provided. The surgical instrument is connectable to the HF generator via a first wire and the neutral electrode is connectable to the HF generator with a second wire. The first and/or second wire is/are equipped with a shield, whereby a decoupling capacitor is disposed at the distal end of each shielded wire. The wire(s) that is (are) equipped with a shield therefore have a decoupling capacitor at their distal end. According to the present disclosure, it is advantageous that the decoupling capacitor is not accommodated in the HF generator housing; instead, the decoupling capacitor is located at the distal end of the wires for connecting the active electrode and the neutral electrode to the HF generator. In this manner, the disadvantages of wire shielding described above are eliminated or at least significantly reduced.

It is preferable to equip the HF surgical device with wires where the shield is earthed/grounded via a ground path (also referred to herein as an "earth path"). It is then especially preferable if the leakage current flowing via the ground path can be detected by means of a current measuring device.

Preferably both the first and the second wire are equipped with a shield such that a decoupling capacitor is then provided at the distal end of the first wire and at the distal end of the second wire. It should be appreciated that that a decoupling capacitor may only be provided at the distal end of the second wire or that a decoupling capacitor may only be provided at the distal end of the first wire.

In another embodiment, it is preferred that the HF surgical device be configured such that the shields on the wires are connectable to the HF generator at a central neutral point via return wires. Preferably, at least one common mode choke is provided in the return wires of the shields to prevent or reduce leakage currents or their interference fields. The advantage of the return wires is that a lower impedance path can be offered to the leakage currents inside the instrument with the result that current paths at points where the patient is in contact with grounded, conductive parts are prevented or reduced.

BRIEF DESCRIPTION OF THE DRAWINGS

Embodiments of the invention are explained in greater detail below with reference to the drawings, in which.

DETAILED DESCRIPTION

Figure 1:
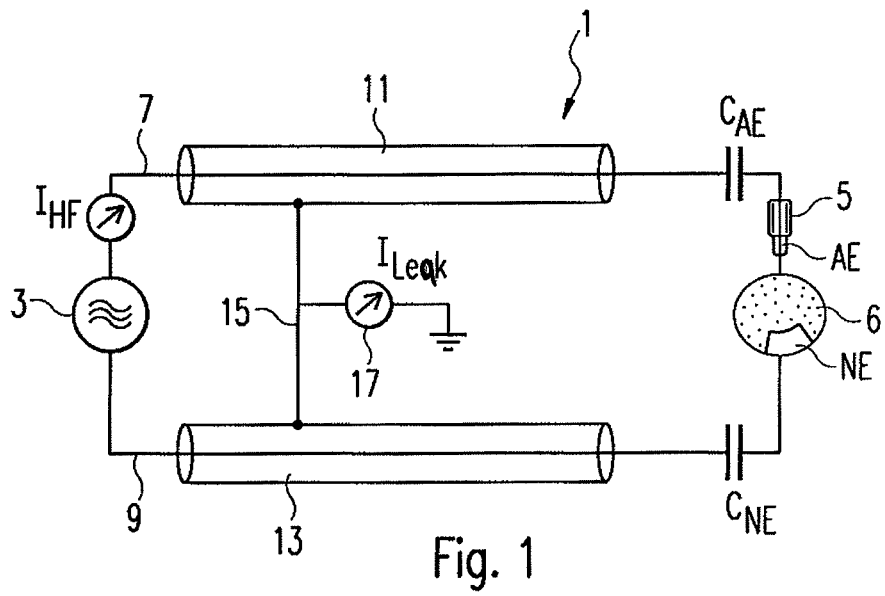
FIG. 1 is a schematic circuit diagram of an HF surgical device according to an embodiment disclosed herein.

FIG. 1 shows a schematic circuit diagram of an HF surgical device 1 according to an embodiment disclosed herein. The HF surgical device 1 has an HF generator 3 and a surgical instrument 5, which may, for example, be a surgical instrument for plasma coagulation of biological tissue. Surgical instrument 5 has an active electrode AE, which is disposed close to a tissue 6 that is to be treated. Furthermore, a neutral electrode NE is provided on the tissue 6 to be treated, said electrode is used to return a current flow through the patient into the HF generator 3 and is in contact with the patient for this purpose.

Active electrode AE of surgical instrument 5 is connected to the HF generator 3 via a first wire 7 for supplying a high-frequency current. Neutral electrode NE is also connected to the HF generator 3 by means of a second wire 9 for returning the current. In the embodiment according to FIG. 1, first wire 7 has a shield 11 and second wire 9 has a shield 13 to minimize the emission of electrical fields by the wires 7, 9, respectively.

Shields 11 and 13 are preferably, as shown in FIG. 1, grounded via a ground path 15 whereby grounding takes place, purely as an example, via common ground path 15. It should be appreciated that separate ground/earth paths for the two shields 11, 13 may also be provided. Furthermore, a current measuring device 17, which measures the leakage current $I_{Leak}$, is provided in the ground path 15. The leakage currents are relatively easy to measure using this configuration since they are only left with a route through the ground of the HF surgical device 1, including the ground of shields 11 and 13; therefore, the leakage currents can be measured virtually in full. With unshielded wires by comparison, there is the problem that the leakage currents will flow on a capacitive path into the patient wires lying outside the instrument and cannot therefore be detected by a sensor system in the instrument. Thus, even if it is not possible to reduce the probability of leakage currents occurring, the leakage currents can at least be detected by the at least one current measuring device 17, proposed herein according to the disclosed embodiment, in the ground paths of the shields.

Figure 2:
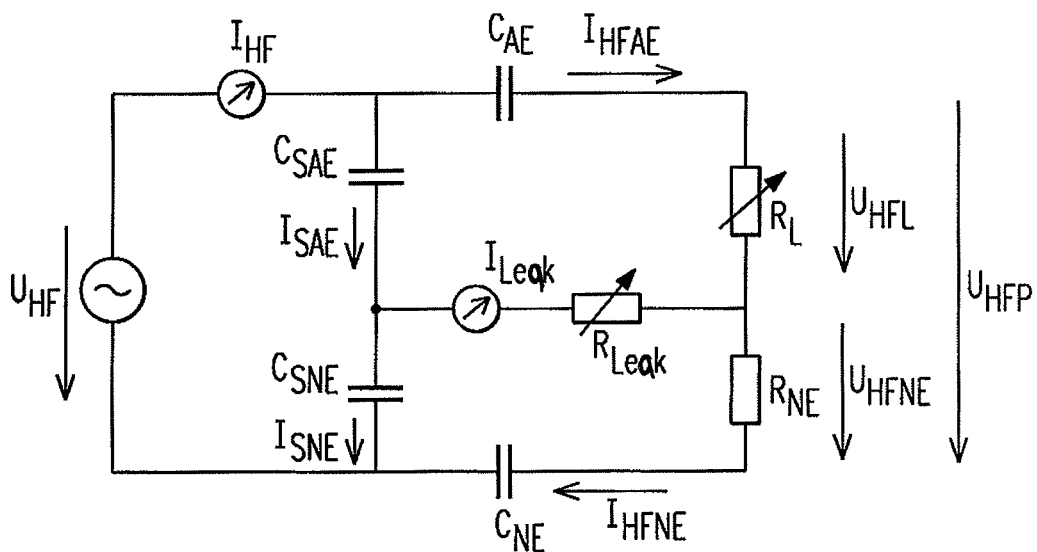
FIG. 2 is an equivalent circuit diagram of the HF surgical device according to FIG. 1.

According to the embodiment of the invention, a decoupling capacitor $C_{AE}$, which prevents the problem of an adverse capacitive voltage divider due to the capacitive load of shield 11, is provided at the distal end of wire 7. The adverse capacitive voltage divider, particularly in the high-resistance load case or in open-circuit operation, reduces HF voltage $U_{HFP}$ (FIG. 2) lying between the active electrode AE and neutral electrode NE in relation to a generator voltage $U_{HF}$ (FIG. 2). This problem is noticeably reduced by moving capacitor $C_{AE}$ to the distal end of first wire 7, particularly in applications where high open-circuit voltages are required, such as during spray coagulation, argon plasma coagulation or similar.

In the embodiment according to FIG. 1, the distal end of wire 9 that is connected to neutral electrode NE also has a decoupling capacitor $C_{NE}$ that makes it possible to further improve the problems associated with shielding. Due to a relatively large surface neutral electrode NE, it is particularly easy to provide a decoupling capacitor there.

Overall it becomes clear that the problems associated with the shields 11 and 13 of wires 7 and 9 can be avoided by moving the decoupling capacitor of the HF generator 3 out of the generator housing and to a distal end of the wires 7 and 9.

FIG. 2 illustrates an equivalent circuit diagram of the HF surgical device 1 according to FIG. 1 which shows the voltage divider described above. The capacitive load of shields 11 and 13 is represented by serial capacitances $C_{SAE}$ and $C_{SNE}$. Load resistance $R_L$ is illustrated in FIG. 2 as a controllable resistor, which is meant to illustrate the various load conditions, in particular a high-resistance load case or open-circuit operation. Furthermore, the impedance of neutral electrode NE is represented by resistor $R_{NE}$. Controllable resistor $R_{Leak}$ makes it clear that the leakage current is variable particularly as a function of resistor $R_L$.

Figure 3:
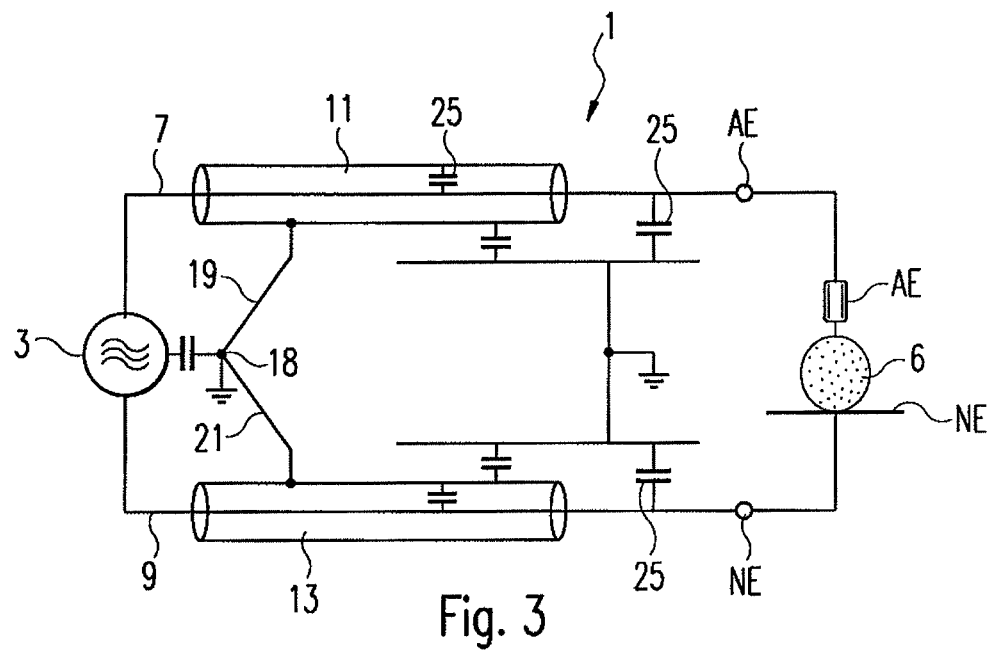
FIG. 3 is a schematic circuit diagram of an HF surgical device according to an embodiment disclosed herein.

FIG. 3 shows a further embodiment of the HF surgical device 1 in which shields 11 and 13 are connected to the HF generator 13 via return wires 19 and 21, respectively. In this case each shield 11, 13 is connected to a return wire 19, 21, which come together in a common central neutral point 18 that is connected to the HF generator 3 via a capacitance. As a result, a lower impedance path inside the HF surgical device 1 is available to the leakage currents, which means that it is highly possible to prevent the occurrence of leakage currents in undesirable places.

Figure 4:
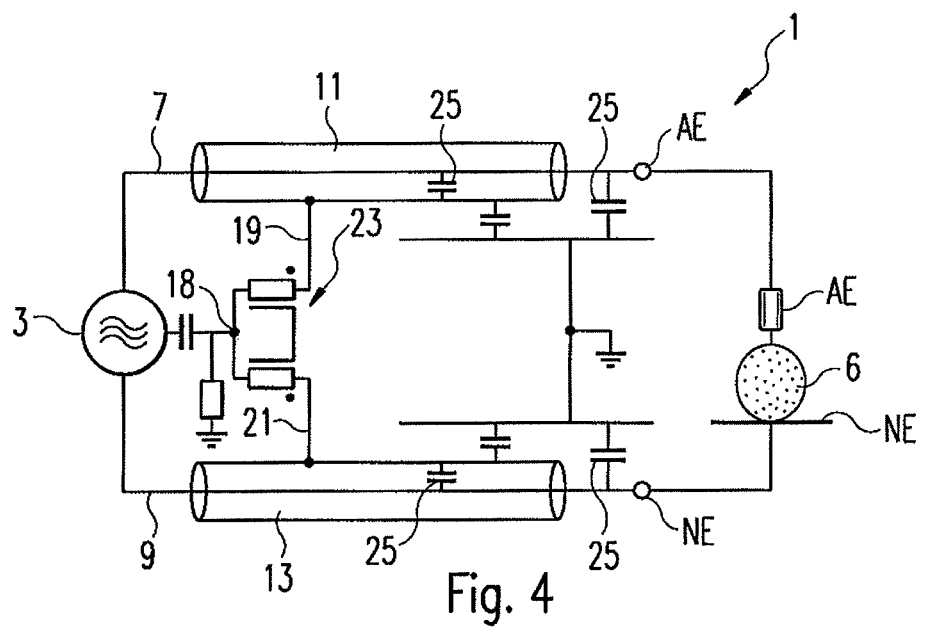
FIG. 4 is a schematic diagram of an HF surgical device according to a further embodiment disclosed herein.

It is particularly preferable to dispose at least one common mode choke 23 in return wires 19 and 21 as shown in FIG. 4. Common mode choke 23 preferably has a plurality of identical windings, which the leakage current in return wires 19 and 21 flows through in the opposite direction such that their magnetic fields cancel each other out in the core of the choke 23. In this way, damping of the electromagnetic interference of the leakage currents is achieved.

FIGS. 3 and 4 further illustrate capacitive couplings, in particular (parasitic) capacitances 25, which arise between the wires and the shields or between the shields and other elements located in the surroundings.

The invention claimed is:

1. A high-frequency (HF) surgical device, comprising:
   an HF generator;
   a surgical instrument having an active electrode and a neutral electrode;
   a first wire connecting the active electrode to the HF generator, said first wire being equipped with a first shield;
   a second wire connecting the neutral electrode to the HF generator, said second wire being equipped with a second shield;
   a first decoupling capacitor disposed at a distal end of the first wire; and
   a second decoupling capacitor disposed at a distal end of the second wire,
   wherein the first and second shields are grounded via a ground path.

2. The HF frequency surgical device of claim 1, wherein the first and second shields are connectable to the HF generator via return wires at a central neutral point.

3. The HF surgical device of claim 2, wherein at least one common mode choke is provided in a return wire.

* * * * *